United States Patent [19]

Raghu et al.

[11] Patent Number: 4,499,283

[45] Date of Patent: Feb. 12, 1985

[54] PROCESS FOR PREPARING 1-SUBSTITUTED-6-N-PROPYL-8-METHYLIMIDAZO[1,5-d]-AS-TRIAZIN-4-(3H)-ONES

[75] Inventors: Sivaraman Raghu, Norwalk; Steven L. Peake, New Canaan, both of Conn.

[73] Assignee: American Cyanamid Company, Stamford, Conn.

[21] Appl. No.: 393,003

[22] Filed: Jun. 28, 1982

[51] Int. Cl.$^3$ .................................... C07D 233/66
[52] U.S. Cl. .................................... 548/343; 564/144; 564/100
[58] Field of Search ................. 564/100, 144; 548/343

[56] References Cited

U.S. PATENT DOCUMENTS 4,328,349  5/1982  Graboyes et al. .................. 548/343

Primary Examiner—Henry R. Jiles
Assistant Examiner—Robert C. Whittenbaugh
Attorney, Agent, or Firm—Edward A. Conroy, Jr.

[57] ABSTRACT

This disclosure describes a novel process for the preparation of 2-(n-propyl)-4-methyl-5-(lower alkanoyl-)imidazoles which are useful as intermediates for the preparation of anti-asthmatic agents.

2 Claims, No Drawings

PROCESS FOR PREPARING 1-SUBSTITUTED-6-N-PROPYL-8-METHYLIMIDAZO[1,5-D]-AS-TRIAZIN-4-(3H)-ONES

BRIEF SUMMARY OF THE INVENTION

This invention relates to a novel method for the preparation of 5-(lower alkanoyl)-4-methyl-2-(lower alkyl)imidazoles (IV) which are the immediate precursors of the corresponding 1-(lower alkyl)-6-(lower alkyl)-8-methylimidazo[1,5-d]-as-triazin-4(3H)-ones (VI). These final products of the novel process of the present invention are highly useful for meliorating asthma and for inhibiting diesterase in mammals. They inhibit the release of mediators (to the extent of 50%) from the human basophil at 13 μM concentration and also protect guinea pigs from anaphylactic shock. In the mouse, they are active both orally and intraperitoneally in inhibiting passive cutaneous anaphylaxis.

The original eight step synthesis of the anti-asthmatic agents (VI), as set forth in U.S. Pat. No. Re. 30,511, proceeded through the key intermediates (IV). These intermediates were prepared in seven steps, three of which [(a) an exothermic mitric acid oxidation, (b) a Grignard reaction, and (c) an environmentally unacceptable chronic acid oxidation] were potentially hazardous for scale-up. It has now been discovered that the novel three step synthesis of the present invention proceeds in high yield and is totally free of all scale-up hazards. The steps involved in the novel process of the present invention may be depicted as follows:

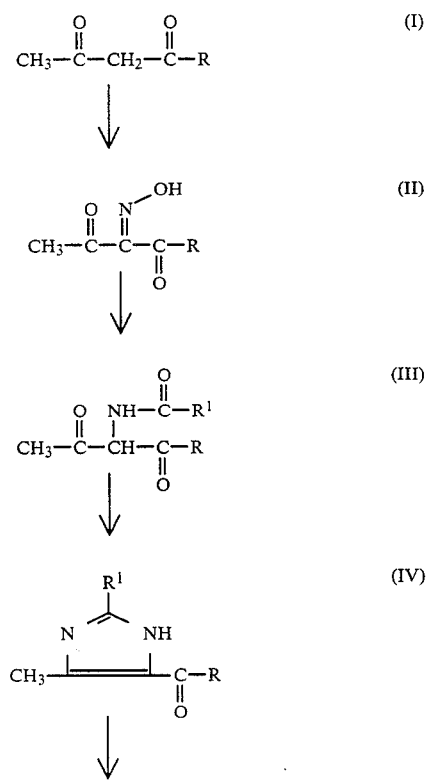

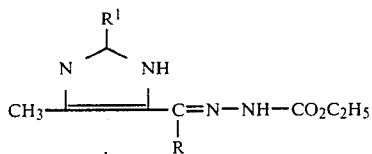

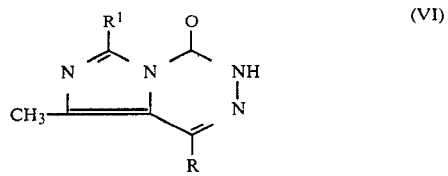

wherein R is methyl, ethyl or n-propyl.

DETAILED DESCRIPTION OF THE INVENTION

In accordance with the above reaction scheme, treatment of a 2,4-alkanedione (I) with sodium nitrite in aqueous sulfuric acid provides the corresponding 3-oximino-2,4-alkanedione of (II) in high yield. The catalytic hydrogenation of (II) with palladium on charcoal as catalyst in the presence of butyric anhydride provides the corresponding 3-butyrylamino-2,4-alkanedione (III) ($R^1$ is n-propyl) also in high yield. Cyclization of (III) to the corresponding 2-(n-propyl)-4-methyl-5-acylimidazoles (IV) is readily accomplished by heating (III) with a suitable ammoniating agent such as ammonium acetate, ammonium chloride, ammonium sulfate, etc. in an inert organic solvent such as formamide toluene, xylene, chlorobenzene, and the like. Condensation of (IV) with ethyl carbazate in n-butanol or diphenyl ether under reflux for several hours provides (V) which may be isolated by evaporation of the reaction solvent. Cyclization of (V) is accomplished in diphenyl ether at 150°–250° C. for 15–45 minutes to provide the anti-asthmatic agents (VI). Isolation of (VI) is achieved by dilution of the reaction mixture with petroleum ether or by extraction of the reaction mixture with 10% aqueous hydrochloric acid. The acid extract is neutralized with potassium carbonate and the product extracted with solvents such as chloroform or ethyl acetate.

The invention will be described in greater detail in conjunction with the following specific examples.

EXAMPLE 1

Preparation of 3-butyramido-2,4-pentanedione

3-Oximino-2,4-pentanedione (38.7 g., 0.3 mol) was dissolved in a solution of butyric acid (30 ml) and butyric anhydride (150 ml., 0.9 mol) contained in a 500 ml. Parr bottle. The 10% Pd on charcoal catalyst (2 g.) was added and the reaction mixture was purged and pressurized with hydrogen to 55 psi, and shaken at room temperature until the theoretical volume of hydrogen had been consumed. The catalyst was separated by filtration and the butyric acid was removed under vacuum. The resulting oily crystals were recrystallized from hot dibutyl ether to give 49.7 g. of product (89.5% yield) m.p. 74°–75° C.

The above procedure was repeated using 3-oximino-2,4-pentanedione and the following anhydrides: acetic, benzoic and propionic.

The above procedure was repeated using butyric anhydride and the following oximes: 3-oximino-2,4-hexanedione, 1-benzoyl-1-oximinoacetone and 5-methyl-3-oximino-2,4-hexandione.

EXAMPLE 2

Preparation of 5-acetyl-4-methyl-2-propylimidazole

3-Oximino-2,4-pentanedione (1.5 g., 11 mmol) was dissolved in butyric acid (2 ml.) and butyric anhydride (10 ml.) contained in a 250 ml. Parr bottle, then 10% Pd on charcoal catalyst (0.1 g.) was added and the reaction mixture was purged and pressurized with hydrogen to 55 psi. After shaking at room temperature for 3 hours, the theoretical amount of hydrogen had been consumed. The catalyst was removed by filtration and 12 ml. of concentrated NH$_4$OH was added to the filtrate. The reaction mixture was heated to 120° C. for 18 hours, then cooled to room temperature. Saturated sodium chloride solution and CH$_2$Cl$_2$ were added. The organic phase was washed twice with 20% HCl solution, and the combined acidic phases were neutralized with concentrated NH$_4$OH and washed with CH$_2$Cl$_2$. The organic phase was dried and the solvent was evaporated to give 0.5 g. of the imidazole as a slight brown oil.

Using the procedure above, the oximes listed in Example 1 were converted into the corresponding imidazoles. In the case of unsymmetrical oximes, the ratio of product isomers was approximately 1:1.

We claim:

1. The process of preparing 3-butyrylamino-2,4-alkanediones of the formula:

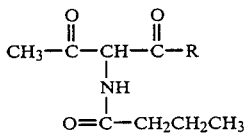

wherein R is methyl, ethyl or n-propyl which comprises hydrogenating a 3-oximino-2,4-alkanedione of the formula:

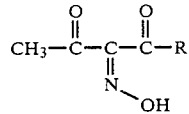

wherein R is an hereinabove defined with palladium on charcoal as catalyst in butyric anhydride as solvent at a temperature of 25°–100° C. for a period of time of 8–24 hours.

2. The process of preparing 5-imidazolyl ketones of the formula:

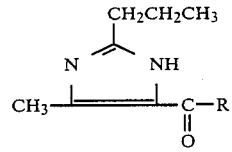

wherein R is methyl, ethyl or n-propyl which comprises condensing a 3-butyrylamino-2,4-alkanedione of the formula:

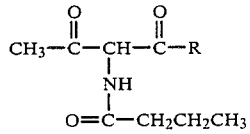

wherein R is as hereinabove defined with an ammoniating agent of the formula: [NH$_4^\oplus$]$_n$[X$^{n\ominus}$] wherein X is an anion and n is an integer from 1 to 4 in an inert organic solvent at a temperature of 100°–150° C. for a period of time of 8–24 hours.

* * * * *